United States Patent
McDermott et al.

(10) Patent No.: US 10,716,916 B2
(45) Date of Patent: Jul. 21, 2020

(54) HIGH LOAD STEERABLE SHAFT AND METHOD FOR CARDIAC CATHETER

(71) Applicant: Creganna Unlimited Company, Galway (IE)

(72) Inventors: Bernard McDermott, Mayo (IE); Adam Szczepanski, Galway (IE)

(73) Assignee: Creganna Unlimited Company, Galway (IE)

( * ) Notice: Subject to any disclaimer, the term of this patent is extended or adjusted under 35 U.S.C. 154(b) by 206 days.

(21) Appl. No.: 15/648,635

(22) Filed: Jul. 13, 2017

(65) Prior Publication Data

US 2018/0021546 A1    Jan. 25, 2018

Related U.S. Application Data

(60) Provisional application No. 62/365,044, filed on Jul. 21, 2016.

(51) Int. Cl.
*A61M 25/01* (2006.01)
*A61M 25/09* (2006.01)

(52) U.S. Cl.
CPC .... *A61M 25/0144* (2013.01); *A61M 25/0133* (2013.01); *A61M 25/0138* (2013.01); *A61M 25/0147* (2013.01); *A61M 25/09* (2013.01); *A61M 25/09033* (2013.01); *A61M 2025/0161* (2013.01); *A61M 2025/09175* (2013.01)

(58) Field of Classification Search
CPC ........ A61M 25/0144; A61M 25/09033; A61M 25/0133; A61M 2025/09175; A61M 25/0147; A61M 25/0138; A61M 2025/0161
See application file for complete search history.

(56) References Cited

U.S. PATENT DOCUMENTS

| | | |
|---|---|---|
| 5,851,212 A | 12/1998 | Zirps et al. |
| 2002/0082585 A1 | 6/2002 | Carroll et al. |

(Continued)

FOREIGN PATENT DOCUMENTS

EP    1457224 A1    9/2004

OTHER PUBLICATIONS

The International Search Report and Written Opinion dated Nov. 16, 2017 for International Application No. PCT/EP2017/068427.

*Primary Examiner* — Amber R Stiles
(74) *Attorney, Agent, or Firm* — Schiff Hardin LLP

(57) ABSTRACT

A tube or skeleton for a steerable catheter includes a cylindrical body structured to permit bending in at least one bending direction and to resist bending in directions transverse to the bending direction. The cylindrical body may include a laser cut metal tube, wires bent and connected to one another, or one or more coiled wires with axial support wires attached to the coil to define one or more bending directions to form bending segments. The skeleton includes axially stiff portions that resist compression when a pull wire is pulled to cause bending movement. The axially stiff portions may include a backbone, an alignment of pivot structures, connected axially extending portions of wire elements, or axially extending support wires or rods. Two or more bending portions may be provided, each with different bending directions. Complex bending shapes may be provided by arranging the segments in rotated positions along the skeleton.

14 Claims, 6 Drawing Sheets

(56) References Cited

U.S. PATENT DOCUMENTS

| | | | |
|---|---|---|---|
| 2003/0199960 A1* | 10/2003 | Paskar | A61M 25/0041 607/122 |
| 2010/0069882 A1 | 3/2010 | Jennings et al. | |
| 2013/0304034 A1* | 11/2013 | Cabiri | A61M 25/0138 604/528 |
| 2014/0135685 A1 | 5/2014 | Kabe et al. | |

* cited by examiner

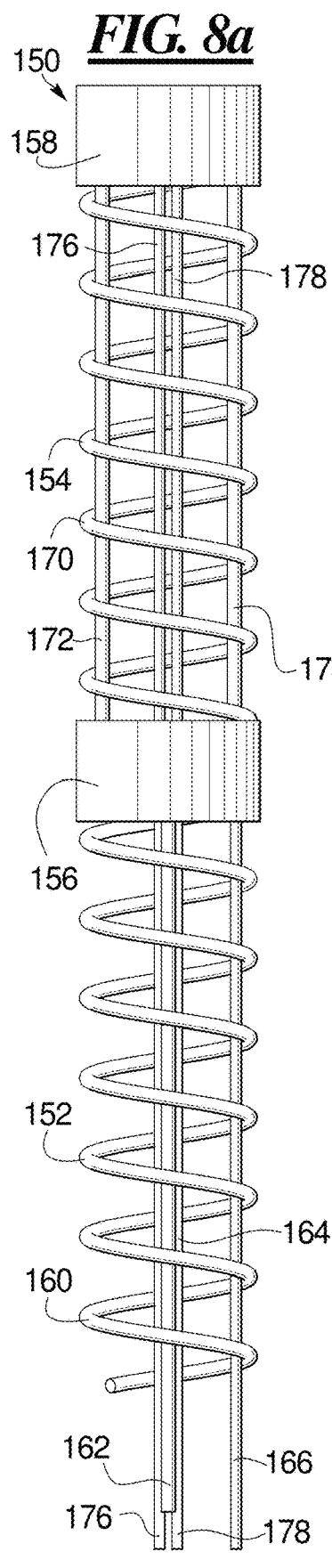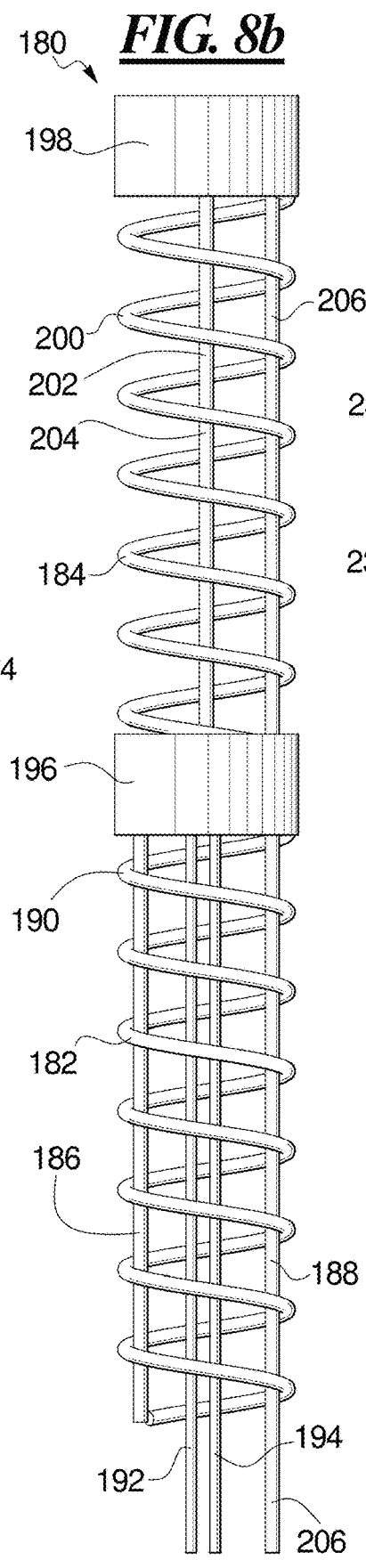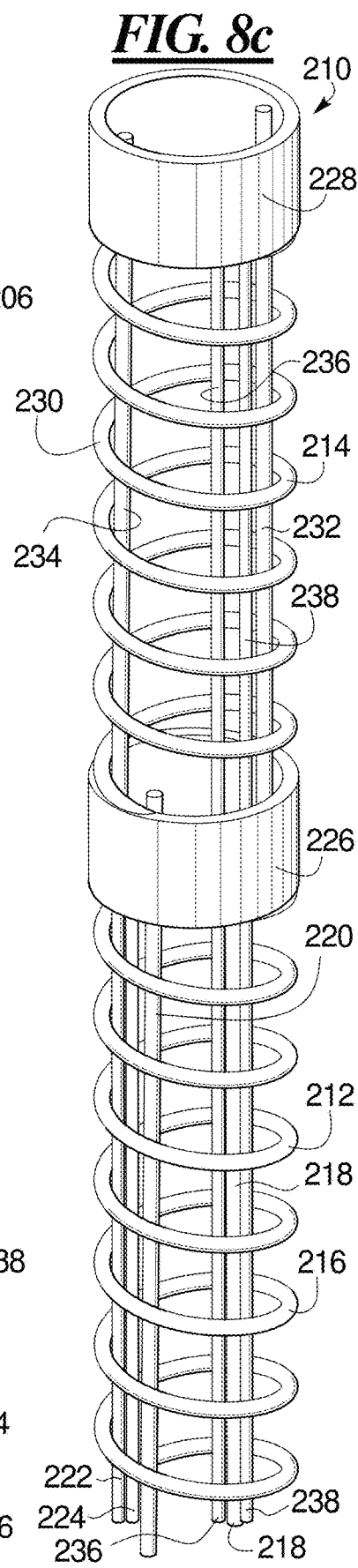

HIGH LOAD STEERABLE SHAFT AND METHOD FOR CARDIAC CATHETER

CROSS REFERENCE TO RELATED APPLICATION

The present application claims the benefit of U.S. Provisional Patent Application Ser. No. 62/365,044, filed on Jul. 21, 2016, which application is incorporated herein by reference.

BACKGROUND OF THE INVENTION

Field of the Invention

The present invention relates generally to an apparatus and method for a catheter, and more particularly to an apparatus and method for a steerable cardiac catheter.

Description of the Related Art

As percutaneous treatments for structural heart diseases continue to evolve, new devices for treatment of both acquired and congenital diseases are becoming available. Access to the patient's anatomy and deliverability of the treatments continue to be primary challenges of the devices. Specifically the nature of the cardiac anatomy and the large diameter of the devices being delivered combine to create these challenges.

The complex structure of cardiac anatomy must be addressed, for example when tracking up to and around the aortic arch for access to the aortic valve; and when crossing the septum and tracking down to the mitral valve or when performing a retrograde access via the aortic arch. These areas of the heart are difficult to reach and difficult to treat using a catheter. These areas of the heart are very often diseased, diffuse and are reached only by tortuous vessels.

Many cardiac treatment devices have large diameters, which must be addressed. Although the current generation of treatment devices have been reduced in size compared to prior generations, the treatment devices currently being used in a minimally invasive fashion are predominately large diameter devices, particularly in relation to treatment of the aortic and mitral valves. There is a real desire to reduce the outside diameter (OD) of the delivery systems.

Existing braid-based steerable catheters are required to have thick walls to limit kinking and axial compression of the shaft during deflections. Typical devices are constructed as follows. A braid and/or coil reinforced shaft is made with an arrangement of pull wires attached to the distal end of the device and running axially along the shaft to the proximal end. These pull wires run through or inside a braided tube. The shaft is constructed with a relatively hard polymer material for the proximal and middle sections and is provided with a softer material in the section which is required to bend. The typically metal wire braid and/or coil reinforcement adds radial strength and kink resistance to the tube along with some axial strength but the composite shaft relies on the strength and hardness of the polymer matrix to a great extent to resist axial compression and kinking. For deflections in a single plane, the pull wire or multiple pull wires run down one side of the tube. When the pull wire is pulled the pulling force reduces the length of the tube on the side of the pull wire, thereby causing the tube to bend in that direction. The material on the side opposite to the pull wire will tend to resist compression but may also decrease in length depending on the deflection load and on the hardness of the matrix material and to some extent on the amount and orientation of the reinforcement.

For two way steerable devices, a second pull wire may be fitted at 180 degrees from the first wire. In this case the device will flex in much the same way as per a single direction device as each wire is loaded, with the flexing caused by each wire being in different directions. The wire opposite the active pull wire may either remain stationary relative to the proximal end or it may move proximally as this side of the deflection section also contracts.

The softer the matrix material in the deflection section, the less the load, or force, that is required on the pull wire to deflect this section. However, the softer the deflection section material is the more likely the deflection section is to kink and for the sheath as a whole to shrink axially. If the sheath is required to deflect while a stiff device is in the lumen of the sheath then the sheath will tend to compress axially before it will start to deflect the device.

Typical solutions to deflecting stiff devices that are within a steerable catheter are to increase the hardness of the matrix material of the catheter, which increases the thickness of the matrix material, and to increase the density of the reinforcing material of the catheter. Increasing the hardness of the material in the deflection section of the catheter leads to higher actuation forces being required to deflect the sheath itself, putting strain on the actuation mechanism, especially at the actuator to distal end attachment of the wire. Increasing the thickness of the material also leads to higher actuation forces and results in a thicker sheath wall. The thicker sheath wall is not ideal as this takes up limited space. Increasing the density of the reinforcement material can also have a negative impact on wall thickness and actuation forces.

SUMMARY OF THE INVENTION

The present invention provides a steerable device for a catheter that includes a hollow tube of generally circular cross section containing a metal support structure to provide enhanced kink resistance and axial stiffness. The support structure can be arranged to allow movement in one or more defined directions. The support structure can also provide an anchorage, or anchor site, for an articulation system which is capable of transmitting high actuation loads to the device.

BRIEF DESCRIPTION OF THE DRAWINGS

FIG. 8a is a front view of a two zone steerable shaft showing steering wires;

FIG. 8b is a side view of the two zone steerable shaft of FIG. 8a;

FIG. 8c is a perspective view of the two zone steerable shaft of FIG. 8a; and

DETAILED DESCRIPTION OF THE PREFERRED EMBODIMENTS

Figure 1:
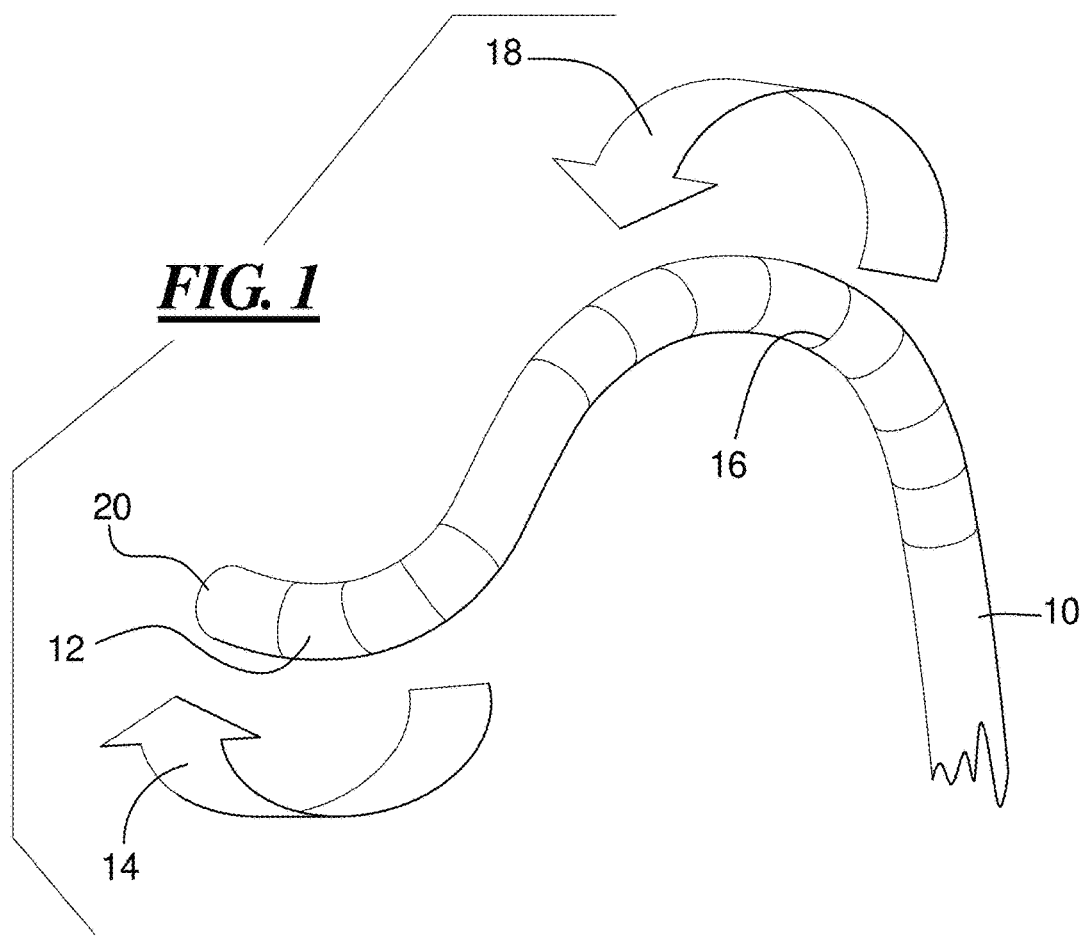
FIG. 1 is a perspective view showing a steerable catheter that has two steering planes.

The present apparatus includes a reinforcing structure or skeleton that is constructed to be stiff in an axial direction but flexible in one or several non-axial directions. The reinforcing structure or skeleton may include a cut metal tube, a formed wire structure, or other reinforcing structure. For example, the cut metal tube may include a laser cut metal tube. The reinforcing structure or skeleton may include hinge structures that permit flexing in at least one direction but that provide axial stiffness to the reinforcing structure. In certain embodiments, the reinforcing structure or skeleton is formed to flex in different bending directions at different bending locations.

The cut metal tube, skeleton, or other reinforcing structure is assembled into a distal/deflectable section of a sheath, over a liner if required, and is jacketed by a polymer material. Pull cables or actuator cables are threaded through lumens inside the cut metal tube, skeleton or other reinforcing structure. The pull cables or actuator cables may be looped around anchorages built into the cut metal tube, skeleton or reinforcing structure at required locations, which may include at the distal end of the deflection section or at intermediate locations in the reinforcing structure, for example at a change of bending direction. The actuator cables may extend in straight lines within the reinforcing structure or may extend along a spiral path or other shaped path within the reinforcing structure to enable the device to deflect in a specific geometry, as accommodated by the skeleton geometry. The cut metal tube, skeleton or reinforcing structure may be assembled over a braided section to give additional support to the tube, if desired.

The cut metal tube, skeleton or other reinforcing structure adds axial strength to the steerable catheter by allowing bending in one or more bending directions through the use of hinges or other structures in the reinforcing structure. The cut metal tube, skeleton or other reinforcing structure provides a continuous axial support along a neutral axis relative to the direction of bending. This means that the axial loads on the catheter are borne/taken by the metal skeleton instead of by a composite polymer and braided structure. The cut metal tube, skeleton or other reinforcing structure of certain embodiments is configured to withstand high axial loads and to resist kink. As the tube or other reinforcing structure bends around a non-compressing neutral axis, the outer surface of the bend elongates and the inner surface reduces in length, accommodated by openings in the cut metal tube or skeleton in certain embodiments. By providing the hinged cut metal tube, skeleton or other reinforcing structure in a catheter, the result is a steerable catheter device in which axial compression is minimized, wall thickness is minimized, kink resistance is increased and actuation loads are decreased.

An advantage to the use of the present cut metal tube, skeleton or other reinforcing structure is that other structures of the steerable catheter are improved. A polymer material may be provided to seal the openings in the cut metal tube, skeleton or other reinforcing structure and to bond the liner to the assembly as its primary or only functions. The polymer material no longer has to be structured to bear the axial loads during bending. As a result, the polymer material can be thin and soft so that it is able to compress and elongate as required on the inside and outside of the bend as the catheter bends through the patient's anatomy.

Using such skeleton reinforcements it is possible to build a catheter device which will allow steering in one plane at a distally located first steering section and allow steering in a separate plane at a second steering section that is proximal to the first steering section. The two steering sections can be steered independently from each other without parasitic motion in either section. In other words, the forces on the catheter to cause steering motion in one of the steering sections would cause little or no steering motion in the other steering section. The skeleton reinforcement in this case would have sections which would allow movement in one plane and restrict movement in the other plane. Although two steering sections are described, it is within the scope of this invention to provide only a single steering section or to provide three or more steering sections in the catheter.

With reference to the figures, FIG. 1 shows a steerable catheter 10 having a first portion 12 that is selectively bendable in a first bending direction or plane as indicated by arrow 14. The catheter 10 has a second portion 16 that is selectively bendable in a second bending direction or plane as indicated by arrow 18. The bending directions or planes may be at an angle to one another, for example, at a 90 degree angle or at another angle to one another. The first and second portions 12 and 16 may be adjacent one another along the axial direction of the catheter or may be spaced from one another along the length of the catheter, for example by a non-bending catheter section that may be disposed between the first and second bending sections. Together, the first and second bending portions 12 and 16, and possibly further bending portions, form a multiple axis bending section. In certain embodiments, the first and second bending sections 12 and 16 are adjacent one another in the multiple axis bending section and the multiple axis bending section is adjacent the free end or distal end 20 of the catheter 10. By providing the multiple axis bending section at or near the distal end 20 of the catheter 10, the user may steer the catheter through complex anatomy of the patient.

Although the illustrated embodiment shows the bending directions bending in directions that are generally perpendicular to one another, other embodiments may provide bending portions configured to bend in bending directions that may be at other angles or relationships to one other. The direction of bending for each bending section is determined by the structure of the bending section and in particular by the structure of the cut tube or skeleton at the bending direction as well as by the pulling wires, as will be apparent from the following.

The illustrated embodiment provides that each of the bending portions 12 and 16 may bend in a curve that follows an arc of a circle. The extent or angle by which each bending section may be bent may be determined by the force exerted on the pulling wire or wires up to a maximum bending angle. The construction of each bending section, in particular the cut tube or skeleton, may determine a maximum bending angle for that bending section. The bending sections may be constructed to bend at a maximum bending angle that is a greater angle or a lesser angle, as desired.

The illustrated embodiment shows that each of the bending sections 12 and 16 may bend at a bending radius; in other words, a tighter or shallower bending curve. The construction of the respective bending section may determine the bending radius about which the bending section may be bent. In particular, the construction of the cut tube or skeleton may determine the bending radius for the bending section.

As apparent to the person of skill in the art, the construction of the bending sections and the positional relationship of the bending sections to one another provides that the bending sections may be selected for different angular relationship between the bending section, different maximum bending angle for each bending section, different bending radius for each bending section, and different spacing along the catheter between each bending section. As a result, a wide variety of complex anatomy may be traversed with the present steerable catheter.

So far, the catheter has been described as having bending sections that are each capable of bending in a single bending plane. The bending sections may be configured to bend in spirals or other complex bending shapes. In certain embodiments, the steerable catheter is constructed to steer in a complex shape such as a spiral shape by constructing the cut tube or skeleton structure to bend in that way. For example, in FIG. 2, a cut metal tube or skeleton 22 of a steerable catheter is shown without the outer covering or inner liner. The tube or skeleton 22 has a first portion 24 that is constructed to bend into a spiral shape when a bending force is exerted on it, such as by a pull wire. A second portion 26 of the tube 22 is bendable in a planar curve shape. In the illustration, the second portion 26 is bendable in nearly in a complete circle in a plane and the spiral bending portion 24 extends out of the plane of the circle. Other complex being shapes are possible as well.

The cut tube or skeleton 22 of the illustrated example is formed of a plurality of segments 28 that may be disposed adjacent one another and arranged sequentially along a length of the catheter. The segments 28 are constructed and shaped to bend in a predefined direction and to bend to a predefined maximum radius. Segments 28 that are arranged adjacent one another that have their bending directions aligned with one another in a common plane will result in a bending portion that bends in the common plane. Segments 28 that are adjacent one another that have their bending directions in different planes with bend in complex ways. For instance, an incrementally rotated bending plane from segment to segment will result in a helical or spiral bending of the catheter. Segments 28 may be grouped together into bending segment groups wherein each bending segment group is configured to undergo a predetermined bending action. The bending segment groups may be positioned adjacent one another along the catheter for bending in the same or different directions or may be spaced from one another with non-bending portions of the catheter between each bending segment group. Other arrangements of bending segments and groups may be provided as well.

Figure 2:
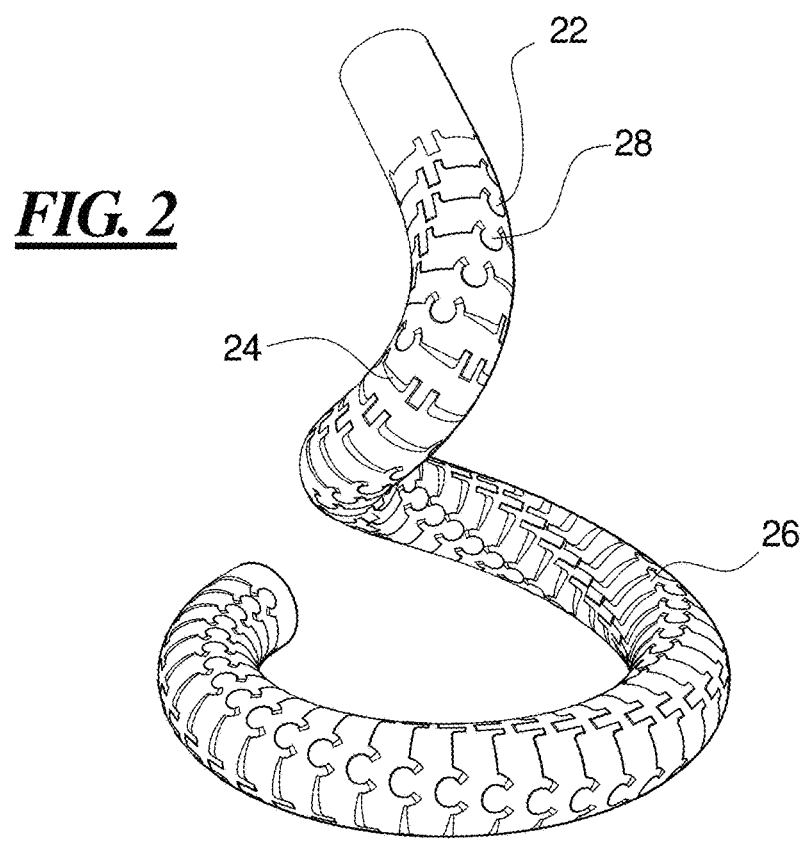
FIG. 2 is a perspective view of a steerable shaft portion for a steerable catheter.

In FIG. 2, the first portion 24 includes a plurality of bending segments 28 having incrementally rotated bending directions from one segment 28 to the next to providing a bending segment group that bends into a spiral or helical bend when subjected to bending forces. The second portion 26 includes a plurality of bending segments 28 that have their bending directions aligned in a common plane and so form a bending segment group that will bend in a coil or circular bend in a plane when subjected to bending forces. Both the first and second portions 24 and 26 may be moved between a bent configuration and a straight configuration by pulling on the respective wires within the catheter. The first and second bending portions 24 and 26 may be moved between the straight and bent conditions separately from one another by pulling on the pull wire for the respective bending portion. Similarly, the bending portions 24 and 26 may be separately moved from the bent condition to the straight condition separately from one another by respective pull wires.

Figure 3:
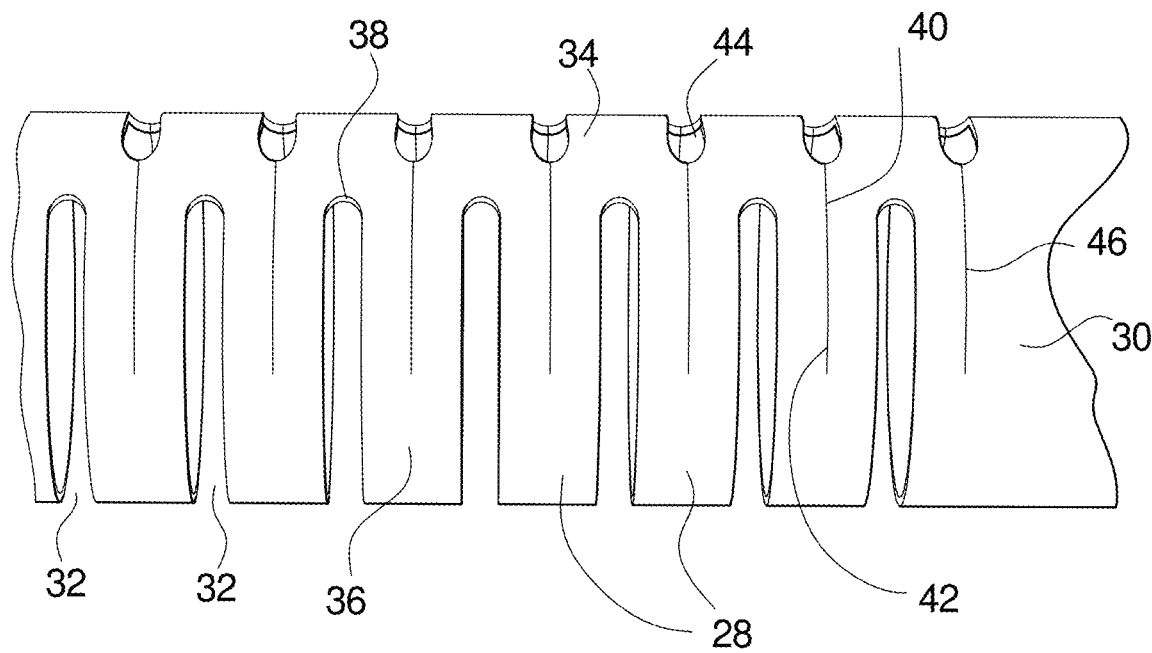
FIG. 3 is an enlarged side view of a portion of a metal steerable shaft for a steerable catheter, the catheter being shown in a straight condition.

FIG. 3 shows an enlarged view of a portion of metal tube or skeleton 30 that forms a bendable portion of a reinforcing structure of a steerable catheter. The metal tube 30 is formed of steel, nitinol, or other material. The tube 30 has been cut with wide and narrows slots, fine slits, and openings in a pattern to permit flexing or bending in a bending direction. The cuts form bending segments 28 that are disposed adjacent one another along the length of the catheter 10. The bending segments 28 of the illustrated embodiment are each configured to bend in a predetermined bending direction. The bending directions of the bending segments 28 of the illustrated example are aligned in a common plane. When a bending force is exerted on the metal tube for example by pull wires, the metal tube will bend in a simple curve in a plane.

The tube 30 includes wide cuts 32 through the tube material. The wide cuts 32 extend in a transverse direction of the tube and extend through more than half of the circumference. In the illustration, the wide cuts 32 extend for more than three quarters of the circumference of the tube. The wide cuts 32 are configured for bending each of the bending segments about the same bending plane by providing that the wide cuts 32 are aligned with one another in an axial direction of the tube. A complex bending portion may be formed by rotating the wide cuts about the tube from one segment to the next, for example.

The portion of the tube 30 not cut by the wide cuts 32 may be referred to as a backbone portion 34. The portions of the tube 30 between the wide cuts 32 may be referred to as the rib portions 36. The wide cuts 32 extend to cut ends 38. The cut ends 38 of each wide cut 32 are aligned in an axial direction along the tube in the illustration. For other bending patterns it may be possible for the wide cuts 32 to be disposed in different positions on the tube, for example with the cut ends 38 changing positions on the tube from one cut to the next, for example. The cut ends 38 need not be in a linear axial arrangement. For example, the backbone portion 34 may extend in a straight line parallel to the axis of the tube, as shown, or the backbone portion 34 may spiral around the tube in a helical pattern or in another pattern or may be formed in other shapes or arrangements. The backbone portion 34 may be oriented along one side of the tube 30 along one portion of the tube 30 and then along another side of the tube 30 for another portion of the tube 30. For example, the different backbone portions 34 may be at an angle from one another about the circumference of the tube.

Between each wide cut 32 is a narrow cut 40. The narrow cuts 40 extend through the backbone portion 34 and through portions of the ribs 36 but do not extend though the ribs 36 at the portion 42 opposite the backbone 34. At the backbone 34, the narrow cuts 40 extend through an opening 44. The openings 44 are aligned along the center of the backbone 34. The uncut portions 42 of the ribs 36 are generally opposite the openings 44. In the illustration, the wide cuts 32 and the narrow cuts 40 are approximately equally spaced along the tube 30 to form the segments. At one end of the tube 30 is an uncut portion 46 that resists bending. The ribs 36 may be wider or narrower to change the radius of the greatest possible bend by the bending portion. The wide cuts 32 may be wider or narrower to change the radius of the greatest possible bend by the bending portion, or a combination of wide or narrow ribs 36 and wide cuts 32 may provide variations in the bending radius. Other cuts or tube characteristics such as tube thickness or material may be changed to vary the bending radius or shape.

The tube 30 of FIG. 3 is shown without an inner liner and without an outer sheath as well as without pull wires which may be provided within the tube 30 to form an operational catheter 10.

The tube 30 provides the skeleton of the catheter that provides load resistance while at the same time permitting bending in one or more predetermined bending directions. The backbone portion 34 resists axial compression of the tube 30, for example when pushing the catheter along a body lumen or when flexing the catheter along a direction not in line with the predetermined bending direction of this bending portion, such as when bending the catheter at a different bending portion that bends in a different bending direction.

Figure 4:
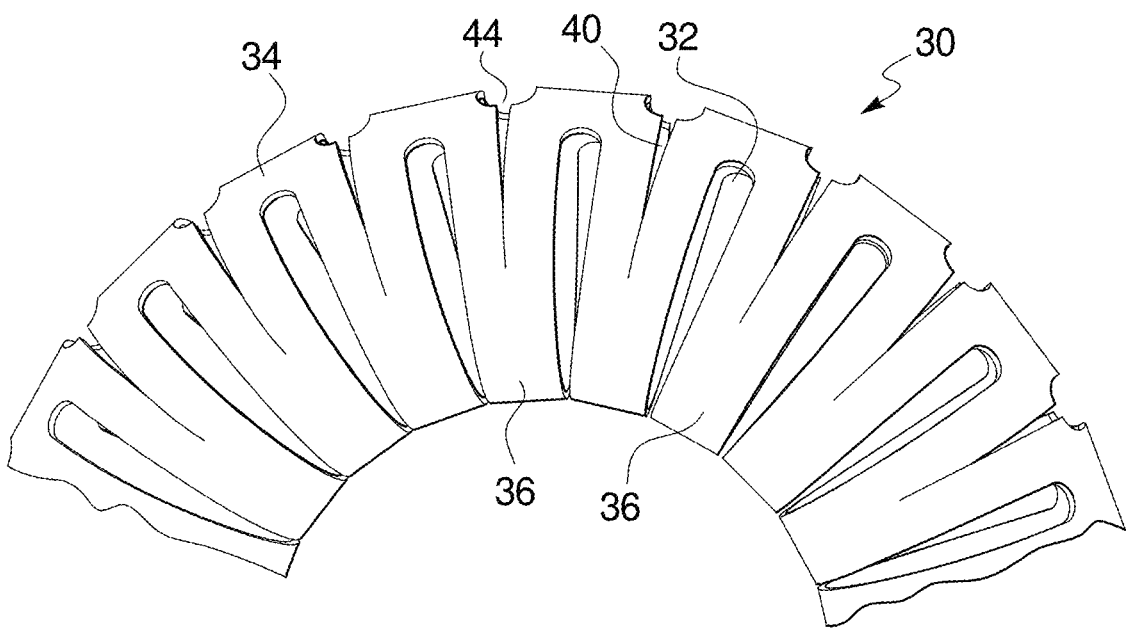
FIG. 4 is an enlarged side view of the metal steerable shaft of FIG. 3 shown in a curved condition.

FIG. 4 shows the tube 30 of FIG. 3 in a flexed or bent position. The bending of the tube 30 results in the ribs 36 being moved closer together at the portions opposite the backbone 34. The middle portions of the wide cuts 32 are narrowed or closed as the tube is bent. The narrow cuts 40 open as the tube is bent, particularly along the backbone 34. The backbone portion 34 flexes during bending of the tube 30. The bent position may be achieved by pulling on a pull wire (not shown) that extends within the tube 30 at a position opposite the backbone portion 34. The pull wire may be provided along the inside of the portions 42. The pull wire, which may be referred to as a bending pull wire, may be provided in a guide or channel within the tube 30 and anchored to the tube 30 at or near a distal end of the tube. Pulling on the pull wire causes the wire to slide within the guide or channel and results in curving or bending of the tube 30 as shown. Release of the pulling tension on the pull wire releases the bending force so that the tube 30 may straighten. A pull wire, which may be referred to as a straighten pull wire, in a guide or channel within the tube 30 extending along the inside surface of the backbone portion 34 may cause the tube 30 to straighten and return to the shape shown in FIG. 3.

The closing of the wide cuts 32 as the bending pull wire is pulled to bend the tube 30 may result in a strong bending force in the bending direction. The closing of the narrow slits 40 when the straighten pull wire is pulled to straighten the tube 30 may result in a less strong straightening force on the tube for the amount of the pulling force exerted by the wire. The resilience of the tube material may assist the tube 30 returning to the straight condition with less or even no pulling force on the straightening pull wire.

Figure 5:
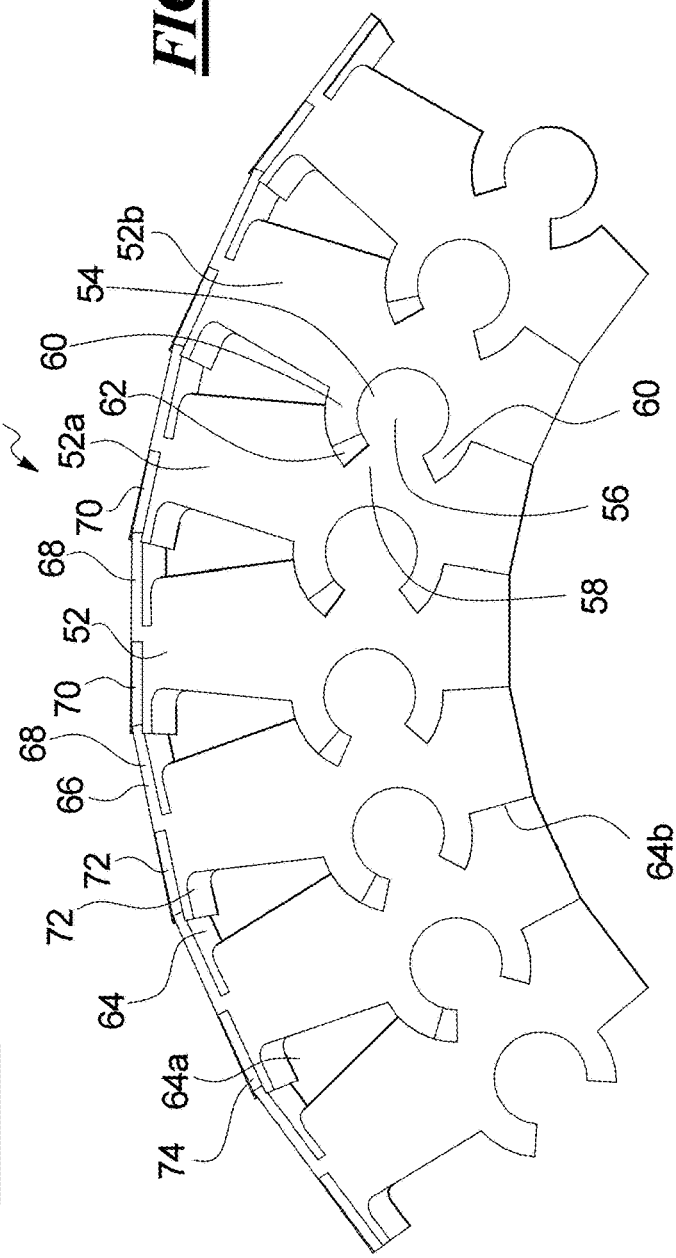
FIG. 5 is an enlarged side view of a metal steerable shaft of a second embodiment.

FIGS. 3 and 4 show a tube 30 in which the bending is accomplished by flexing of the backbone portion 34 of the tube material. Tubes or skeletons may be provided that do not require flexing of the tube material when bending. In FIG. 5 is shown a tube 50 in which segments 52 are formed with pivot structures 54 along generally one or more sides of the tube 50. The pivot structures 54 are shaped to permit adjacent segments 52 to pivot relative to one another. In the illustrated example, the pivot structure 54 may include a semi-circular portion 56 on a base 58 that extends from a segment 52a. An adjacent segment 52b has a crescent shaped portion 60 that wraps part way around the semi-circular portion 56 yet leaves a gap 62 between one or both ends of the crescent shaped portion 60 and the base 58 to form the complementary portion of the pivot structure 54. As the tube 50 bends, the crescent shaped portion 60 rotates around the semi-circular portion 56, providing a pivot between the segments 52a and 52b. The gaps 62 accommodate the pivoting movement by widening or narrowing as the crescent shaped portion 60 moves about the semi-circular portion 56.

Each segment 52 is provided with a semi-circular portion 56 at one end and a crescent shaped portion 60 at the other end, with the adjacent segments being coupled together at the connected pivot structures 54. The pivot structures 54 are aligned in a direction that controls the bending shape of the tube, either in a line that is generally parallel to the axis of the tube for bending in a plane or in a helix or other arrangement along the tube for more complex bending. A liner and sheath is provided on the segments which may keep the segments from moving radially relative to one another and which may keep the pivot structures 54 coupled together.

A similar pivot structure 54 may be provided on the other side of the tube 50. For example, the pivot structures 54 may extend along to opposing sides of the tube 50, either diametrically opposed from one another or possibly offset from a diametrical opposition. The pivot structures 54 provide resistance to bending when forces are exerted along the line of the pivot structure but permit bending when bending forces are exerted along a portion of the tube spaced from the pivot structure 54.

The pivoting movement between the segments 52 is accommodated not only by the gaps 62 but also by openings 64 between the segments 52 at portions away from the pivot structures. In the illustrated example, the opening 64a has opened and the opening 64b has closed as a result of flexing of the tube 50. Flexing in the opposite direction would cause opening 64a to close and opening 64b to open, at least to a greater extent than shown in this illustration.

Each of the segments 52 is provided with an alignment guide portion 66 at a position spaced circumferentially from the pivot structures 54. The alignment guide portion 66 includes an axially extending center portion 68 extending from a segment 52a that is received in an axially extending slot 70 in a next adjoining section 52b. On each side of the axially extending slot 70 are axially extending side projections 72 that extend toward the adjoining segment 52. The axially extending side projections 72 are disposed on opposite sides of the axially extending center portion 68 regardless of the extent of the bend in the catheter. Channels 74 extend into the segment 52 on both sides of the axially extending center portion 68. The axially extending side projections 72 extend into the channels 74 when the catheter bends so that the alignment guide portion 66 is at an inside of the bend, the axially extending side projections 72 moving out of the channels 74 when the alignment guide portion 66 is at an outside of a bend, as shown in FIG. 5. In certain embodiments, there are alignment guide portions 66 on both opposite sides of the tube 50, approximately one quarter of the way around the tube 50 from the pivot structures 54.

The illustrated pivot structures 54 and alignment guide portions 66 permit bending of the tube 50 by pivoting movement between the segments 52 while maintaining the segments 52 aligned with one another. Other structures that permit pivoting movement between the segments and that maintain the segments in alignment during pivoting are also possible and are within the scope of this invention.

Figure 6A:
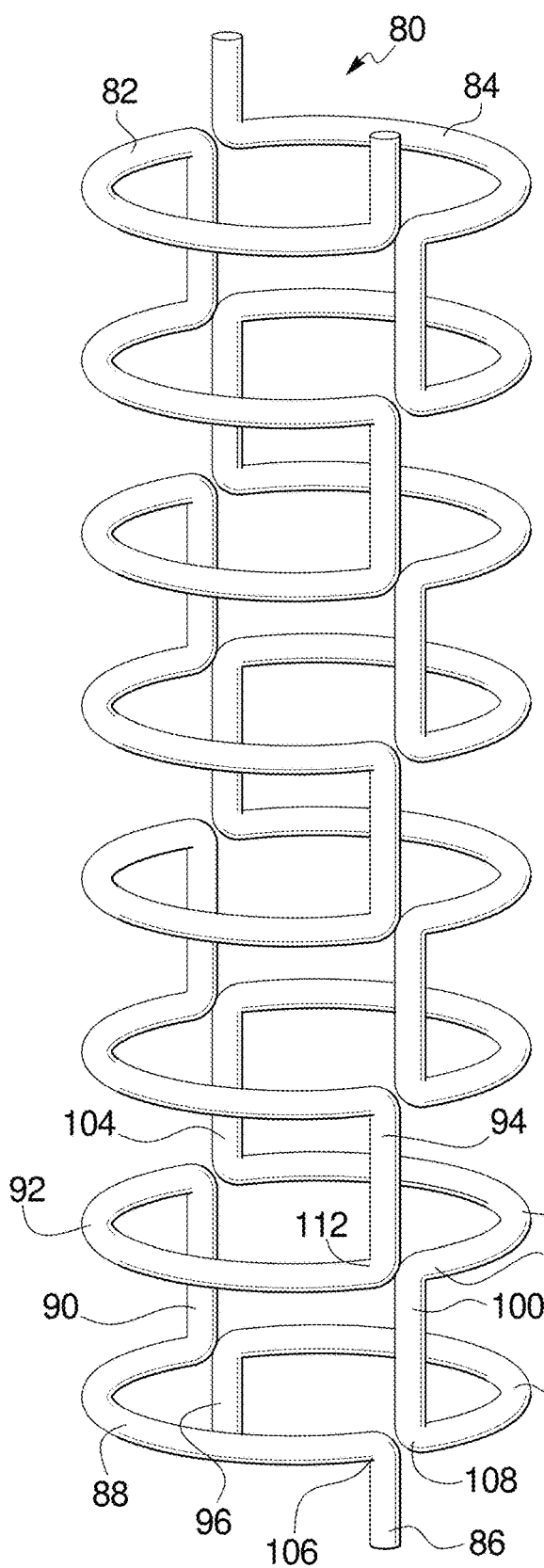
FIG. 6a is a side perspective view of a two wire steerable shaft.

In FIG. 6a is shown another embodiment of the skeleton 80 for a bendable catheter Like the other catheter skeletons or tubes shown, the skeleton 80 has a preferred bending direction for each segment and a direction that resists bending. The structures that resist bending may also provide resistance to axial compression for the tube or skeleton. The resistance to axial compression in the bending portion permits accurate control of the bending section as well as accurate control of other bending portions that are joined to the instant bending portion. This provides particular advantage when the other bending portions that bend in a different bending direction than the instant bending portion Like the other skeleton or tubes shown, the skeleton defines a bending direction that may be either in a plane or in a complex shape such as a helix or other shape. The non-bending directions, in other words the directions toward which the catheter does not bend at the bendable portion, are generally, although not necessarily transverse to the bending direction. For example, the bending direction may be along a diameter of the cylindrical tube or skeleton and the non-bending direction may be generally perpendicular to the bending direction diameter.

In FIG. 6a, the skeleton is formed of two lengths of wire 82 and 84 that are formed into complementary shapes and joined to one another to form a cylinder. The wire 82 is formed with a vertical portion 86 that connects to a horizontal portion 88. The horizontal portion 88 curves along an arc and connects at its opposite end to a second vertical portion 90. The second vertical portion 90 connects at its opposite end to a second horizontal portion 92 that curves in an arc that is parallel to the first horizontal portion 88. The opposite end of the second horizontal portion 92 is connected to a further vertical portion 94. In similar fashion, each vertical portion is connected to a horizontal arc-shaped portion and each horizontal arc-shaped portion is connected to a vertical portion. The terms vertical and horizontal relate to the view as shown in the figure, and do not necessarily correspond to the orientation of the catheter in the physical world.

Each horizontal portion, such as 88 and 92, is disposed in a respective plane that is transverse to the axis of the cylinder formed by the skeleton 80, each of the planes of the respective horizontal portions being parallel when the catheter is unbent. Bending of the catheter will result in the planes of the horizontal portions becoming non-parallel. Each second vertical portion, such as 86 and 94, are aligned with one another along a line that is generally parallel to the axis of the cylindrical skeleton 80 and runs along a side wall of the cylinder. The vertical portions, for example, 90 and 94 are on opposite sides of the cylindrical skeleton. In certain embodiments, the vertical portions are diametrically opposite one another along opposite sides of the skeleton.

The second wire 84 is shaped in a similar shape as the first wire 82. For example, the wire 84 has a vertical portion 96 that connects to an arc-shaped horizontal portion 98. The horizontal portion 98 connects at its opposite end to a second vertical portion 100. The second vertical portion 100 connects at its opposite end to a second horizontal portion 102. The second horizontal portion 102 connects at its opposite end to a further vertical portion 104. The wire 84 is similarly shaped along its further extent. The second wire 84 is approximately a mirror image of the first wire, or more particularly a rotational mirror image. For example, a vertical portion, for example portion 90, of the first wire 82 has a corresponding vertical portion, for example portion 100, of the second wire 84 at a diametrically opposite position and orientation. A horizontal portion, for example portion 92, of the first wire 82 has a corresponding horizontal portion, for example portion 102, of the second wire at a diametrically opposite position and orientation.

The first and second wires 82 and 84 are joined to one another to form the cylindrical skeleton 80. The junction between each vertical portion and the adjoining horizontal portion of each wire is connected to a corresponding junction of the other wire. For example, a junction 106 between the vertical portion 86 and the horizontal portion 88 of the first wire 82 is connected to a junction 108 between a horizontal portion 98 and a vertical portion 100 of the second wire 84. The junction 110 between the vertical portion 100 and the horizontal portion 102 of the second wire is connected to a junction 112 between the horizontal portion 92 and the vertical portion 94 of the first wire 82. The connections of the wires 82 and 84 at the junctions may be made by welding, connectors, adhesive, or other connection means. The wires 82 and 84 may be made of steel, nitinol or other materials.

Connections between the junctions continue along both sides of the cylindrical skeleton 80 so that the vertical portions of the first and second wires 82 and 84 are connected together. The connected vertical sections form a compression resistant portion of the skeleton 80 that runs along the two generally opposite sides of the cylinder. The compression resistant portions formed by the joined vertical sections prevent flexing of the catheter in a direction toward the vertical portions when pull is exerted by a pull wire. However, a pull wire positioned at the horizontal portions, for example approximately midway along the length of the arc-shaped horizontal portions will cause bending of the catheter in a bending direction toward the side having the horizontal portions and generally perpendicular to the vertical portions.

The skeleton 80 is configured to bend in two opposite directions, a first bending direction toward the horizontal portions of the first wire 82 and a second bending direction toward the horizontal portions of the second wire 84. Pull wires (not shown) are anchored and positioned to run along an inside of the cylindrical skeleton generally at the midpoint of the horizontal portions. The pull wires may be provided on one or both sides of the skeleton for bending the catheter in one or both bending directions. The skeleton 80 is provided with a liner within the skeleton and a sheath on the outsize of the skeleton 80 when provided in the catheter.

Figure 6B:
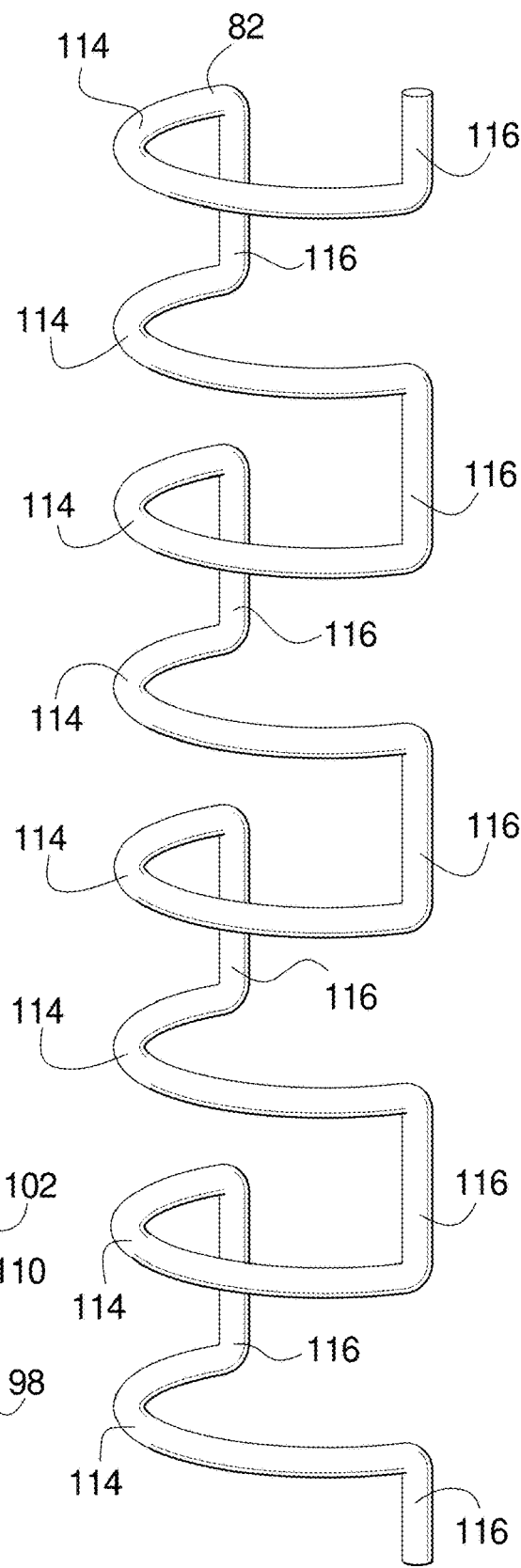
FIG. 6b is a side perspective view of a single wire steerable shaft.

FIG. 6b shows the first 82 prior to being joined to the second wire. The first wire 82 has every arc-shaped horizontal portion, designated generally as 114, disposed generally parallel to one another and, in certain embodiments, equally spaced from one another. The horizontal portions 114, which may also be termed circumferential arc portions, are each curved about approximately one half of a circle, or about 180 degrees. The corresponding horizontal portions of the second wire 84 provide the other half of the circle when the two wires 82 and 84 are joined to one another. The circular parts formed by the joined circumferential arc portions 114 of the two wires 82 and 84 are segments in this embodiment. The segments are connected to one another by the joined vertical portions, designated generally as 116 in FIG. 6b.

The bendable portion formed by the skeleton of FIGS. 6a and 6b may be used as the sole bendable section in a catheter or with other bendable portions in a catheter, for example with bendable portions having other bending directions. Although the alignment of the segments and vertical sections of the illustrated example shows the structure to provide bending within a plane, the vertical sections may be offset from on another at each adjacent segment, for example, by rotating the structure of the wire at each adjacent segment, so as to provide a complex bending shape such as a helical bending shape.

Figure 7A:
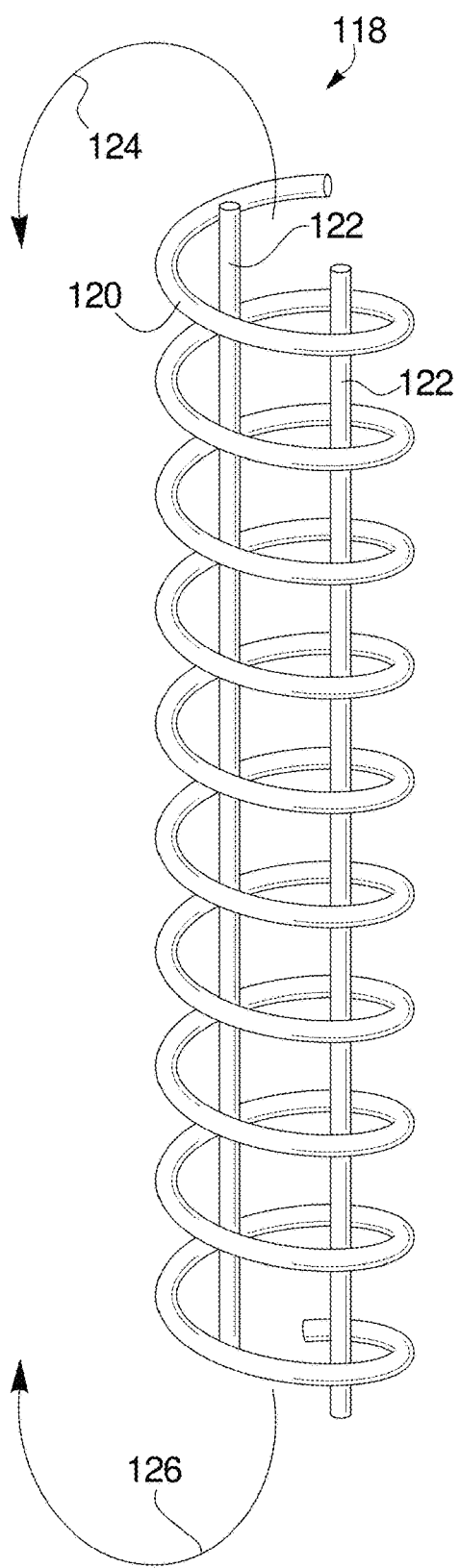
FIG. 7a is a side perspective view of a coiled wire steerable shaft.

In FIG. 7a, a bending portion 118 includes a wire 120 formed into a coil having a cylindrical shape. In the illustrated embodiment, two axial support wires or rods 122 are joined to the coil 120 by being connected at each loop of the coil 120 along two sizes of the cylinder. For example, the axial wires 122 may extend along opposite sides of the coil 120 at the inside surfaces of the coil 120. The joining of the axial wires 122 to the coiled wire 120 may be by welding, connectors, adhesive or other joining means. The axial support wires 122 are constructed to resist axial compression and to be axially stiff but are configured for bending in a transverse direction. The axial support wires 122 may be formed of nitinol, steel, or other materials.

A pulling wire may be mounted within the coil 120 extending along the inside or outside of the coil 120 at a position approximately midway between the axial wires 122, either on one or both sides of the cylindrical coil 120 and anchored at an end of the coil or other anchor location. The axial wires 122 resist the pulling force of the pulling wire while the loops of the coiled wire 120 between the axial wires 122 will move toward one another in response to the pulling force, resulting in bending of the catheter in a direction shown by arrows 124 and 126. The illustrated skeleton 118 may also bend in a direction opposite the arrows 124 and 126 if a pull wire is provided along the opposite side. In this embodiment as well as others, the pull wires may be provided within a channel or other passageway to permit sliding movement of the wire relative to the skeleton and liner during bending.

Figure 7B:
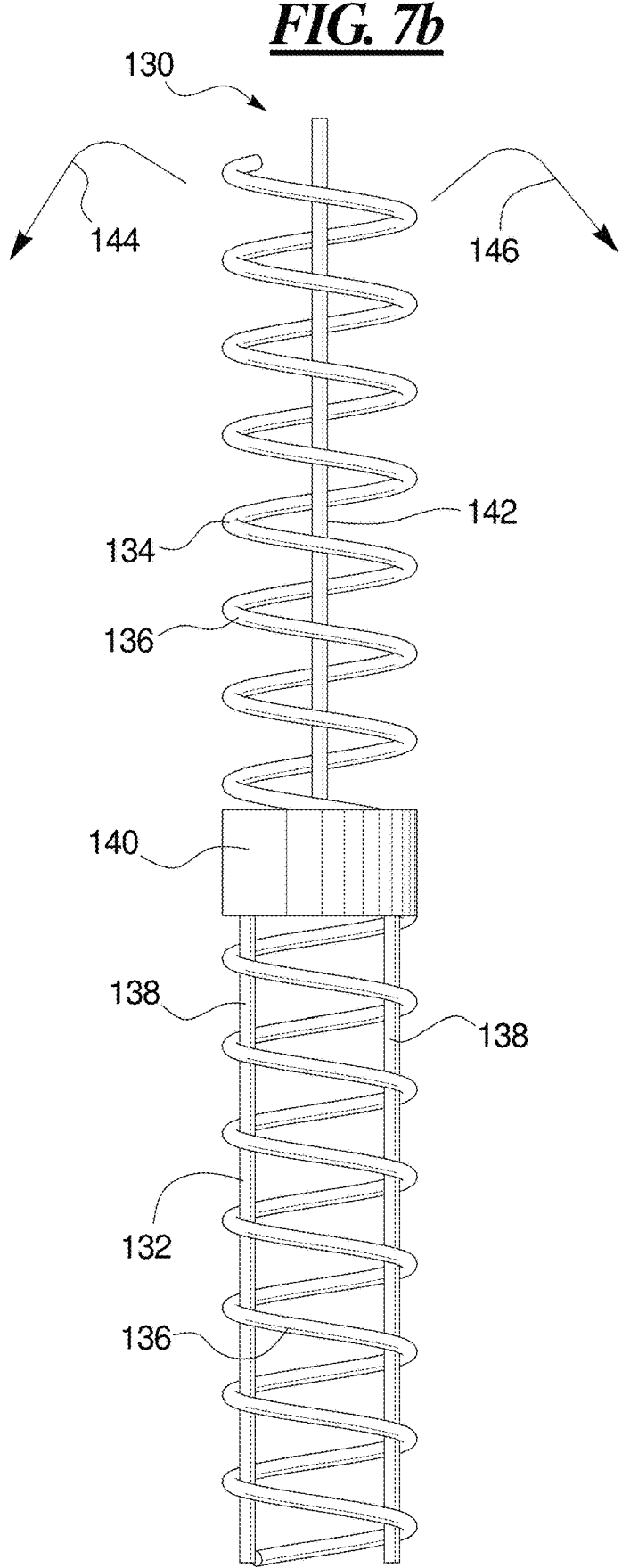
FIG. 7b is a side view of a coiled wire steerable shaft having a first portion for bending in a first direction and a second section for bending in a second direction.

FIG. 7b shows an embodiment of a skeleton 130 having two bending portions 132 and 134. Each of the bending portions 132 and 134 is formed by a coiled wire 136, which may be the same coiled wire 136 for both bending portions 132 and 134 or may be separate coiled wires for the two bending portions. Each bending portion 132 and 134 and two axial support wires. The axial support wires 138 are provided in the lower bending portion 132 on opposite sides of the coiled wire 132, the axial wires 138 being fastened within the right and left sides of the coil 136 in the illustration. The bending portion 132 is capable of bending out of and into the page.

The second bending portion 134 is attached to the first bending portion 132 by a ring 140. The ring 140 may be of steel or other material and formed with an inside diameter matching the outside diameter of the coiled wire 136. The coiled wire 136 may be joined to the ring 140 by welding or by other attachment means.

The second bending portion 134 has two axial support wires 142 connected within the inner surface of the coiled wire 136 just as in the first bending portions 132 but rotated by 90 degrees relative to the first bending portions 132. The second axial support wire 142 is behind the first axial support wire 142 in the view of FIG. 7b. As a result of the rotated structure of the second bending portion 134, the second bending portion 134 may bend in the plane of the drawing, as indicated by arrows 144 and 146. For example, a pull wire mounted along the inside of the coiled wire 136 to the left side of the skeleton 130 relative to the view of FIG. 7b may be pulled to move the second bending portion 134 in the direction of the arrow 144. Releasing the tension on the pull wire may permit the second bending portion 134 to return to the straight position as shown, depending on patient anatomy, for example. Pulling on a pull wire mounted along the right hand side of the skeleton relative to the FIG. 7b will cause the second bending portion 134 to bend in the direction of the arrow 146 and releasing the tension on the pull wire may permit the second bending portion 134 to straighten, depending on the anatomy of the patient, for example.

The pulling force exerted on the pull wires that move the second bending portion 134 in the bending directions 144 or 146 may only cause the second bending portion 134 to bend without resulting in bending of the first bending portion 132. For example, if the second bending portion 134 is located distally of the first bending portion 132 and the pull wires for the second bending portion 134 pass through the first bending portion 132, the pulling force on a pull wire for the second bending portion 134 will be applied to both the first and second bending portions 132 and 134. The application of the pulling force on the second bending portion 134 may result in the second bending portion bending but the axial support wires 138 of the first bending portion 132 may resist the pulling force and reduce or eliminate compression/or and bending of the first bending portion 132 from the pull wires of the second bending portion 134.

Of course, pull wires for bending the first bending portion 132 need not extend through the second bending portion 134 but may end at or near the ring 140 in embodiments where the second bending portion is distally located of the first bending portion 132. Any pulling force on the pull wires for the first bending portion 132 will not reach the second bending portion 134. However, even if the pull wires for the first bending portion 132 do extend through the second bending portion 134, the pull wires for the first bending portion 132 would be generally aligned along the axial support wires 142 of the second bending portion 134 and thus resist compression and bending in the second bending portion 134 when the pull wires are subjected to a pulling force. For example, it is contemplated that a further bending portion may be provided distally of the second bending portion 134, the further bending portion being structured like the first bending portion 132 so that both the first and the further bending portions bend into or out of the page while the second bending portion remains unbent by the force of the pulling wires of the first and further bending portions. Other complex configurations may be provided as well. Although the pulling forces on the pull wires have been described as applied separately for the different bending portions, it may provide useful for the pulling forces to be applied together for the two bending portions. For example, the pulling force on the wire of one bending portion may be applied simultaneously as the pulling force on the other bending portion or the pulling forces may be applied sequentially. The bending actions of the different bending portions 132 and 134 operate separately from one another, with one bending portion being capable of bending without causing bending or compression in the other bending portion.

FIG. 8a shows an embodiment of a skeleton 150 that includes a first bending portion 152 and a second bending portion 154 joined by a ring 156. The distal end of the second bending portion 154 includes a second ring 158. The first bending portion 152 includes a coiled wire 160 and two axial support wires 162 and 164 that are mounted on the inner surface of the coiled wire 160 at opposite sides thereof. The axial support wire 164 is behind the axial support wire 162 in the figure. The first bending portion 152 of the illustrated embodiment includes a first portion pull wire 166 that is anchored at the distal end of the first bending portion 152 and that slides freely along the inside surface of the coiled wire 160 so that pulling force on the pull wire 166 will cause bending of the first bending portion 152 in the direction of the pull wire 166. Bending of the first bending portion 152 is in the plane of the drawing toward the right hand side, relative to the drawing FIG. 8a.

The second bending portion 154 includes a coiled wire 170, which may be a separate wire from the coiled wire 160 or the coiled wire 160 and the coiled wire 170 may be formed together of the same wire as a unitary structure. The second bending portion 154 has two axial support wires 172 and 174 connected along opposite inside surfaces of the coiled wire 170. The second bending portion 154 of the illustrated embodiment has two pull wires 176 and 178 that are anchored at or near the end of the second bending portion 154 and that extend along the inside surface of the coiled wire 170 at opposite sides thereof. The pull wires 176 and 178 may slide along the inside of the coiled wire 170 to cause the second bending portion 154 to bend in the direction toward the pull wire that is exerting the pulling force. The skeleton 150 is configured for bending in two bending directions at the second bending portion 154 and for bending in a single bending direction at the first bending portion. The bending directions of the second bending portion 154 are into and out of the page relative to the drawing. The bending directions of the bending portions 152 and 154 are directed approximately one quarter the way around the cylindrical skeleton 150 from each other, although other bending direction arrangements may be provided.

FIG. 8b shows an alternate embodiment of a skeleton 180 having a first bending portion 182 and a second bending portion 184. The first bending portion 182 includes two axial support wires 186 and 188 fastened along opposite inside surfaces of a coiled wire 190. Two pull wires 192 and 194 are anchored at the distal end of the first bending portion 182 for exerting pulling forces to bend the first bending portion 182 in two opposite directions into and out of the page relative to the drawing.

A ring 196 is provided between the first bending portion 182 and the second bending portion 184. A second ring 198 is provided at the distal end of the second bending portion 184. The second bending portion 184 has a coiled wire 200 within which is mounted two axial support wires 202 and 204, the axial support wire 204 being positioned behind the axial support wire 202 in the figure. A second portion pull wire 206 is anchored at the distal end of the second bending portion 184 and extending along an inside surface of the coiled wire 200 midway between the two axial support wires 202 and 204. The second portion pull wire 206 extends through the first bending portion 182. In each of the embodiments shown in FIGS. 8a and 8b the pull wires extend from the proximal end of the bending portions. The pull wires will extend a distance greater than shown, for example all the way to an operating mechanism for the user to exert a pulling force on the pull wires. The bending portions, on the other hand, will be mounted at a distal end of a catheter tube.

FIG. 8c shows an embodiment of a skeleton 210 that has a first bending portion 212 and a second bending portion 214. The first bending portion 212 includes a coiled wire 216 with two axial support wires 218 and 220 connected opposite one another within the coiled wire 216. Two pull wires 222 and 224 are disposed side-by-side along the first bending portion 212. Bending of the first bending portion 212 is accomplished by pulling on both pull wires 222 and 224. The bending direction is to the left and out of the page relative to the figure.

A first ring 226 is provided at the distal end of the first bending portion 212, the second bending portion 214 being joined to the first ring 226. A second ring 228 is at the distal end of the second bending portion 214. The second bending portion 214 has a coiled wire 230 and two axial support wires 232 and 234 mounted within the coiled wire 230 on opposite sides thereof. The second bending portion 214 is controlled by two pull wires 236 and 238. The pull wires 236 and 238 are arranged side-by-side along one side of the cylindrical coiled wire 230. The pull wires 236 and 238 are anchored to the second ring 228 or other location at the distal end of the second bending portion 214. By exerting a pulling force on the two pull wires 236 and 238, the second bending portion 214 bends in the direction of the pull wires 236 and 238. In the illustration, the second bending portion 214 will bend out of and to the right relative to the page. The two pull wires 236 and 238 are arranged on either side of the axial support wire 218 of the first bending portion 212. A channel for the two pull wires 236 and 238 may be formed along the opposite sides of the axial support wire 218. As noted above, the pull wires 222, 224, 236 and 238 extend in a proximal direction from the bending portions 212 and 214. The dual pull wires provide the potential for exerting a stronger bending force than a single pull wire embodiment.

Figure 9:
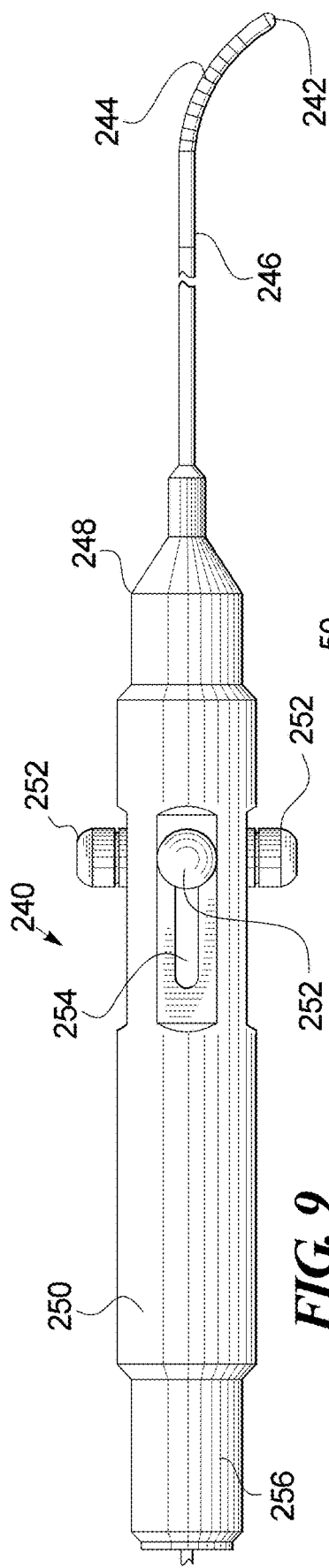
FIG. 9 is a side view of a prior art steerable catheter and handle assembly.

FIG. 9 shows a prior art catheter device 240 as shown in European patent application EP 0 980 693A1. The present bendable portions may be used in a device similar to this catheter device. The catheter includes a distal end 242 that is connected to a bendable portion 244. The bendable portion 244 may be replaced by a bendable portion according to the present invention. The bendable portion 244 is connected to a catheter shaft 246 that may be as long as necessary to perform the medical procedure. The catheter shaft 246 may include a sheath over the outer surface and a liner within the inner surface and may be hollow to accommodate a guide wire or other tool or device. The catheter shaft 246 is mounted in a chuck 248 that is at the end of a handle 250. The pull wires in the catheter device 240 are connected to sliders 252 that move within channels 254 to exert pulling force on the respective pull wires and thereby steer or bend the bendable portion 244. The sliders 252 may each correspond to a pull wire. Fewer or more sliders may be provided as needed. A receiving collar 256 may be provided at the opposite end of the handle 250 through which may be inserted wires, tools or other devices as needed. The catheter device 240 is but one example of a device which may use the present bendable or steerable shaft device.

Thus, there are shown reinforcing structure examples of laser cut tubes, skeletons or other structures that are steerable or bendable in one or more directions but that include structural features that resist compression as a result of pulling forces exerted to cause the tube or skeleton to bend. The bending direction or directions of the tube or skeleton is directed and controlled by the structural features of the device.

The skeleton structure can be constructed from metal wires, can be stainless steel or Nitinol or others. The nitinol wire structure can be heat-set into a suitable geometry.

Another innovation is the attachment of the actuator wires to the skeleton in such a way as to maximize their load carrying capability. The actuator mechanism uses wire cables for increased flexibility and the wire cables run from the proximal end, are looped around features at the actuation points on the skeleton tube and return to the proximal end. Both ends are secured together and the load is fed in through this pair. Typical devices have the actuators welded to a control ring at the distal end. This control ring feeds the loads into the sheath. By welding the wires or cable, the effective cross section of the actuators is reduced dramatically as the heat affected zone reduces the strength of the wires significantly resulting in a load capability below that of an unwelded wire. looping the wires over a feature at the proximal end retains the strength of the actuators.

Thus, there are shown and described a laser cut tube with integral hinges to allow movement in a single plane. Also shown and described a wire formed skeleton, which may be made of heat set nitinol.

A tube or skeleton for a steerable catheter is provided including a cylindrical body having a structure of a bending portion that permits bending in at least one bending direction and that resists bending in directions transverse to the at least one bending direction. The cylindrical body may be formed of a laser cut metal tube that is shaped to provide bending segments, of wires that are bent and connected to one another to provide bending segments, or of one or more coiled wires with axial support wires attached to the coil to define one or more bending directions and thereby form bending segments. Each of the embodiments includes axially stiff structures that resist compression when a pull wire within the tube or skeleton is pulled to cause bending movement. The axially stiff structures may include a backbone, an alignment of pivot structures, connected axially extending portions of wire elements, or axially extending support wires or rods. Two or more bending portions may be provided in the tube or skeleton, each with different bending directions. Complex bending shapes may be provided by arranging the segments in rotated positions along the bending portion.

In a first aspect, a skeleton for a catheter is provided, comprising: a bending portion including a cylindrical body having a first end and a second end, the bending portion being structured to bend in a predetermined bending direction, the bending portion including a plurality segments arranged sequentially adjacent one another in the bending portion; an axial support structure extending along at least one side of the cylindrical body, the axial support structure being flexible to permit being in the predetermined bending direction but being resistant to compression in an axial direction; the bending portion being configured for receiving a pull wire extending along an inside wall of the cylindrical body in a direction of the predetermined bending direction with the pull wire anchored at the first end and extending beyond to the second end for receiving a pulling force, the bending portion being configured to bend in the predetermined direction in response to the pulling force exerted on the pull wire.

In a second aspect, a skeleton of the first aspect is provided, wherein the bending portion is formed of a metal tube.

In a third aspect, a skeleton of the second aspect is provided, wherein the metal tube includes a backbone portion as the axial support structure and a plurality of wide cuts into the metal tube opposite the backbone structure to form the segments.

In a fourth aspect, a skeleton of the second aspect is provided, wherein the metal tube includes pivot structures as the axial support structure, the pivot structures connecting each of the segments to one another, the pivot structures being disposed on opposite sides of the cylindrical body.

In a fifth aspect, a skeleton of the first aspect is provided, wherein the bending portion includes first and second wires formed into segments, the axial support structure including axially extending portions of the first and second wires joined to one another.

In a sixth aspect, a skeleton of the first aspect is provided, wherein the bending portion includes a coiled wire providing the cylindrical body, and wherein the axial support structures includes at least one axial support wire or rod connected to the coiled wire along a side of the cylindrical body.

In a seventh aspect, a skeleton of the sixth aspect is provided, wherein the axial support structures includes two axial support wires or rods extending along opposite sides of the cylindrical body and connected to the coiled wire.

In an eighth aspect, a skeleton of the first aspect, further comprising: a ring connected to the first end of the cylindrical body.

In a ninth aspect, a skeleton of the first aspect, wherein the bending portion is a first bending portion, and further comprising: a second bending portion connected to the first bending portion, the second bending portion having a predetermined bending direction different than the predetermined bending direction of the first bending portion.

In a tenth aspect, a skeleton of the ninth aspect, further comprising: a ring connected between the first and second bending portions.

In an eleventh aspect, a skeleton of the first aspect, wherein the structures of the segments are rotated about the axis of the cylinder relative to one another to provide a complex bending shape for the bending portion.

In a twelfth aspect, a method for guiding a catheter, comprises: bending a portion of a cylindrical body having a first end and a second end, the bending occurring at bending portion structured to bend in a predetermined bending direction, the bending portion including a plurality segments arranged sequentially adjacent one another in the bending portion; axially supporting at least one side of the cylindrical body, the axially supporting permitting flexing to permit bending in the predetermined bending direction but being resistant to compression in an axial direction; and receiving a pull wire extending along an inside wall of the bending portion of the cylindrical body in a direction of the predetermined bending direction with the pull wire anchored at the first end and extending beyond to the second end for receiving a pulling force, the bending portion being configured to bend in the predetermined direction in response to the pulling force exerted on the pull wire.

Although other modifications and changes may be suggested by those skilled in the art, it is the intention of the inventor to embody within the patent warranted hereon all changes and modifications as reasonably and properly come within the scope of his contribution to the art.

We claim:

1. A skeleton for a catheter, comprising:
    a bending portion including a cylindrical body having a first end and a second end, the bending portion being structured to bend in a predetermined bending direction, the bending portion including a plurality of segments arranged sequentially adjacent one another in the bending portion,
        the plurality of segments each defining a wide cut transverse to an axis of the cylindrical body, the wide cuts each extending more than half way into the cylindrical body, each of the wide cuts ending at first and second wide cut ends,
        the plurality of segments each defining a narrow cut transverse to the axis of the cylindrical body, the narrow cuts each extending more than half way into the cylindrical body, the narrow cuts being disposed between two adjacent ones of the plurality of wide cuts, portions of the plurality of wide cuts overlapping portions of the plurality of narrow cuts in an axial direction of the cylindrical body;
        the plurality of segments each including a rib, the ribs being disposed between two adjacent ones of the plurality of wide cuts, one of the plurality of narrow cuts extending into each of the ribs, ones of the plurality of narrow cuts extending between adjacent ones of the first wide cut ends and between adjacent ones of the second wide cut ends;

an axial support structure extending along at least one side of the cylindrical body, the axial support structure being flexible to permit bending in the predetermined bending direction but being resistant to compression in an axial direction, the axial support structure being disposed between the first and second wide cut ends of each of the plurality of wide cuts; and the bending portion being configured for receiving a pull wire extending along an inside wall of the cylindrical body in a direction of the predetermined bending direction with the pull wire anchored at the first end and extending beyond to the second end for receiving a pulling force, the bending portion being configured to bend in the predetermined direction in response to the pulling force exerted on the pull wire.

2. A skeleton as claimed in claim 1, wherein the bending portion is formed of a metal tube.

3. A skeleton as claimed in claim 2, wherein the metal tube includes a backbone portion as the axial support structure and a plurality of wide cuts into the metal tube opposite the backbone structure to form the plurality of segments.

4. A skeleton as claimed in claim 3, wherein the plurality of wide cuts extend in a transverse direction of the tube and extend through more than half of the circumference of the tube.

5. A skeleton as claimed in claim 4, wherein the plurality of wide cuts extend for more than three quarters of the circumference of the tube.

6. A skeleton as claimed in claim 3, wherein the plurality of wide cuts are spaced equally from one another along a length of the tube.

7. A skeleton as claimed in claim 3, wherein the plurality of wide cuts are aligned with one another in an axial direction of the tube.

8. A skeleton as claimed in claim 7, wherein the plurality of wide cuts end at cut ends, and wherein the cut ends are aligned in an axial direction along the tube and the backbone portion extends along a side of the tube parallel to an axis of the tube.

9. A skeleton as claimed in claim 8, wherein the backbone portion is a first backbone portion defining a first bending direction and further comprising a second backbone portion having a second bending direction.

10. A skeleton as claimed in claim 3, wherein the backbone portion defines a plurality of narrow cuts extending transverse to the axis of the tube, each one of the plurality of narrow cuts being disposed between two adjacent ones of the plurality of wide cuts.

11. A skeleton as claimed in claim 10, wherein the plurality of wide cuts define ribs between adjacent ones of the plurality of wide cuts, and wherein the plurality of narrow cuts extend from the backbone portion into the ribs, the plurality of narrow cuts ending before a portion of the ribs opposite the backbone.

12. A skeleton as claimed in claim 10, wherein the backbone portion defines a plurality of openings, the plurality of openings being aligned along a center of the backbone, the plurality of openings including a widening of the plurality of narrow cuts along a center of the backbone regardless of whether the skeleton is in a bent or straight position, the plurality of narrow cuts extending from the plurality of openings.

13. A skeleton as claimed in claim 10, wherein the plurality of wide cuts and the plurality of narrow cuts are equally spaced in an axial direction along the tube.

14. A skeleton as claimed in claim 3, wherein the plurality of wide cuts are offset from one another in a pattern around the tube to cause the tube to bend in a non-linear bending movement when subject to a bending force.

* * * * *